(12) United States Patent
Olson et al.

(10) Patent No.: US 9,295,247 B2
(45) Date of Patent: Mar. 29, 2016

(54) METHOD OF USING INSECT BAIT STATION

(71) Applicant: ECOLAB USA INC., St. Paul, MN (US)

(72) Inventors: Joelle F. Olson, Shoreview, MN (US); Kelly J. Herrera, St. Paul, MN (US); James J. Tarara, Woodbury, MN (US); L. Mitch Lark, St. Paul, MN (US); Paul M. Sanderson, Prior Lake, MN (US)

(73) Assignee: ECOLAB USA INC., St. Paul, MN (US)

( * ) Notice: Subject to any disclaimer, the term of this patent is extended or adjusted under 35 U.S.C. 154(b) by 0 days.

(21) Appl. No.: 14/741,884

(22) Filed: Jun. 17, 2015

(65) Prior Publication Data
US 2016/0015019 A1 Jan. 21, 2016

Related U.S. Application Data

(62) Division of application No. 12/486,918, filed on Jun. 18, 2009, now Pat. No. 9,089,122.

(60) Provisional application No. 61/074,266, filed on Jun. 20, 2008.

(51) Int. Cl.
*A01M 1/20* (2006.01)
*A01M 1/02* (2006.01)
*A01N 1/00* (2006.01)

(52) U.S. Cl.
CPC .............. *A01M 1/2005* (2013.01); *A01M 1/02* (2013.01); *A01M 1/023* (2013.01); *A01M 1/2011* (2013.01)

(58) Field of Classification Search
CPC ......... A01M 1/00; A01M 1/02; A01M 1/023; A01M 1/10; A01M 1/20; A01M 1/2005; A01M 1/2011
USPC ................................ 43/123, 107, 131, 132.1
See application file for complete search history.

(56) References Cited

U.S. PATENT DOCUMENTS 2,051,800 A * 8/1936 Lindecker ........... A01M 1/2005
  43/121
2,652,807 A * 9/1953 Washburn .............. A01K 63/02
  119/203

(Continued)

FOREIGN PATENT DOCUMENTS

CA      2323057     *  9/1999
DE   10108179 A1   *  9/2002  .............. A01M 1/02

(Continued)

OTHER PUBLICATIONS

C. Montes, Maintenance of a Laboratory Colony of Cimex lectularius Using an Artificial Feeding Technique, Journal of Medical Entomology, Jul. 2002, vol. 39 No. 4, pp. 675-679.*

*Primary Examiner* — Darren W Ark
(74) *Attorney, Agent, or Firm* — Amy J. Hoffman

(57) ABSTRACT

A device for controlling blood-feeding insects is disclosed. The device includes a membrane containing a solution suitable for consumption by blood-feeding insects wherein the solution is comprised of a base, the base selected from the group consisting of up to 70 wt % NaCl in water, phosphate buffer, citric acid in water, and sodium lauryl sulfate in water; and wherein the solution has a pH of between about 6 and 8. An additional active ingredient may be added to the solution. The solution may be referred to as liquid bait. The membrane is suitable for blood-feeding insects to pierce or puncture in order to feed. A method of exterminating or controlling blood feeding insects is also disclosed along with novel bait solutions.

19 Claims, 1 Drawing Sheet

(56) References Cited

U.S. PATENT DOCUMENTS

| | | | | |
|---|---|---|---|---|
| 2,773,175 A * | 12/1956 | Levy | A01K 63/003 | 362/124 |
| 2,949,882 A * | 8/1960 | Thomas, Jr. | A01K 63/02 | 119/203 |
| 2,989,856 A * | 6/1961 | Telkes | F25D 3/00 | 165/47 |
| 3,168,887 A * | 2/1965 | Bodell | A01K 63/02 | 119/201 |
| 3,236,206 A * | 2/1966 | Willinger | A01K 63/02 | 119/203 |
| 3,401,671 A * | 9/1968 | Axelrod | A01K 63/02 | 119/203 |
| 3,565,041 A * | 2/1971 | Brooks | A01K 63/02 | 119/203 |
| 3,728,988 A * | 4/1973 | Shapero | A01K 63/02 | 119/201 |
| 3,958,393 A * | 5/1976 | Whitener | B65D 85/50 | 383/33 |
| 4,043,073 A * | 8/1977 | Basile | A01M 1/02 | 43/131 |
| 4,168,591 A * | 9/1979 | Shaw | A01M 1/023 | 43/124 |
| 4,459,188 A * | 7/1984 | Rutherford | C01D 3/14 | 159/47.1 |
| 4,554,189 A * | 11/1985 | Marshall | F25D 3/08 | 428/11 |
| 4,747,701 A * | 5/1988 | Perkins | B65F 1/0006 | 220/495.01 |
| 4,761,314 A * | 8/1988 | Marshall | F25D 3/08 | 428/11 |
| 4,869,017 A * | 9/1989 | Bird | C12N 1/12 | 435/257.1 |
| 5,117,777 A * | 6/1992 | Takasugi | A01K 63/02 | 119/203 |
| 5,150,906 A * | 9/1992 | Molitor | A63B 37/0003 | 156/145 |
| 5,188,832 A * | 2/1993 | Mehlhorn | A61K 31/53 | 424/405 |
| 5,216,976 A * | 6/1993 | Marinkovich | A01K 61/00 | 119/200 |
| 5,241,778 A * | 9/1993 | Price | A01M 1/023 | 43/112 |
| 5,292,504 A * | 3/1994 | Cardin | A01N 53/00 | 424/405 |
| 5,311,696 A * | 5/1994 | Gauthier | A01M 1/04 | 43/113 |
| 5,359,808 A * | 11/1994 | Fitsakis | A01M 1/2016 | 43/131 |
| 5,464,837 A * | 11/1995 | Mehlhorn | A61K 31/53 | 424/405 |
| 5,480,155 A * | 1/1996 | Molitor | A63B 37/0003 | 156/145 |
| 5,603,176 A * | 2/1997 | Eddins | G09F 19/08 | 40/406 |
| 5,657,576 A * | 8/1997 | Nicosia | A01M 1/023 | 43/107 |
| 5,707,638 A * | 1/1998 | Losel | A01N 25/34 | 424/405 |
| 5,737,870 A * | 4/1998 | Thind | A01M 1/026 | 43/107 |
| 5,919,100 A * | 7/1999 | Boehm | A63B 37/0003 | 273/DIG. 20 |
| 6,033,771 A * | 3/2000 | Heffelfinger | B29C 47/0021 | 264/173.14 |
| 6,053,635 A * | 4/2000 | Anderson | B31B 19/86 | 383/10 |
| 6,088,949 A * | 7/2000 | Nicosia | A01M 1/023 | 43/107 |
| 6,357,170 B1 * | 3/2002 | Bordes, Jr. | A01M 1/026 | 43/121 |
| 6,374,536 B1 * | 4/2002 | Washburn | A01M 1/026 | 43/131 |
| 6,389,740 B2 * | 5/2002 | Perich | 424/409 | |
| 6,463,693 B1 * | 10/2002 | Weisner | A01M 1/04 | 43/119 |
| 6,467,215 B1 * | 10/2002 | Nelson | A01M 1/023 | 43/107 |
| 6,557,492 B1 * | 5/2003 | Robohm | A01K 63/02 | 119/203 |
| 6,582,712 B2 * | 6/2003 | Pullen | C07G 17/00 | 424/405 |
| 6,601,337 B1 * | 8/2003 | McKenney, Sr. | A01M 1/02 | 43/132.1 |
| 6,718,689 B1 * | 4/2004 | Kolibas | A01M 1/2005 | 43/131 |
| 6,920,716 B2 * | 7/2005 | Kollars, Jr. | A01M 1/023 | 43/107 |
| 6,986,323 B2 * | 1/2006 | Ayers | A01K 61/00 | 119/200 |
| 7,591,099 B2 * | 9/2009 | Lang | A01M 1/023 | 43/107 |
| 7,743,552 B2 * | 6/2010 | Borth | G01N 33/68 | 422/402 |
| 7,836,851 B2 * | 11/2010 | Gergely | A01K 63/04 | 119/201 |
| 7,905,048 B2 * | 3/2011 | Borth | G01N 33/68 | 43/124 |
| 8,110,608 B2 * | 2/2012 | Herrera | A01N 41/02 | 514/709 |
| 8,505,489 B2 * | 8/2013 | Lyngstad | A01K 63/02 | 119/201 |
| 8,661,728 B2 * | 3/2014 | Borth | G01N 33/68 | 43/124 |
| 8,808,721 B2 * | 8/2014 | Banfield | A01M 1/026 | 424/405 |
| 9,089,122 B2 * | 7/2015 | Olson | A01M 1/023 | |
| 2003/0152603 A1 * | 8/2003 | Johnson | A01M 1/023 | 424/405 |
| 2003/0188695 A1 * | 10/2003 | Robohm | A01K 63/02 | 119/203 |
| 2006/0219184 A1 * | 10/2006 | Wilson | A01K 63/02 | 119/203 |
| 2006/0254123 A1 * | 11/2006 | Su | A01M 1/026 | 43/132.1 |
| 2008/0096458 A1 * | 4/2008 | Andersen | A63H 3/24 | 446/26 |
| 2008/0205800 A1 * | 8/2008 | Su | B29C 47/0021 | 383/109 |
| 2009/0107409 A1 * | 4/2009 | Yu | A01K 63/02 | 119/203 |
| 2009/0145019 A1 * | 6/2009 | Nolen | A01M 1/023 | 43/121 |
| 2009/0145020 A1 * | 6/2009 | McKnight | A01M 1/023 | 43/123 |
| 2009/0159010 A1 * | 6/2009 | Spartz | A01K 63/00 | 119/200 |
| 2009/0223115 A1 * | 9/2009 | Lang | A01M 1/023 | 43/114 |
| 2010/0212213 A1 * | 8/2010 | Hope, III | A01M 1/026 | 43/123 |
| 2010/0322990 A1 * | 12/2010 | Burke | A01N 25/04 | 424/405 |
| 2011/0041385 A1 * | 2/2011 | Faham | A01M 1/023 | 43/123 |
| 2011/0047860 A1 * | 3/2011 | Black | A01M 1/02 | 43/123 |
| 2011/0072712 A1 * | 3/2011 | Black | A01M 1/02 | 43/123 |
| 2011/0203159 A1 * | 8/2011 | McKnight | A01M 1/023 | 43/123 |
| 2012/0100098 A1 * | 4/2012 | Herrera | A01N 41/02 | 424/84 |
| 2012/0190268 A1 * | 7/2012 | Mustafa | A63H 33/18 | 446/46 |
| 2012/0321587 A1 * | 12/2012 | Rosen | A01N 41/02 | 424/84 |
| 2013/0112151 A1 * | 5/2013 | Mizrachi | A01K 61/007 | 119/223 |
| 2014/0130399 A1 * | 5/2014 | Halahmi | A01M 1/2005 | 43/131 |

(56) References Cited

U.S. PATENT DOCUMENTS

2014/0290647 A1 * 10/2014 Salvinelli ............ A61K 31/7004
                                                      128/200.14

FOREIGN PATENT DOCUMENTS

| | | | | | |
|---|---|---|---|---|---|
| EP | 0 292 948 | * | 11/1988 | | |
| FR | 2852490 | A1 * | 9/2004 | .......... | A01M 1/2005 |
| GB | 2443701 | A * | 5/2008 | ............ | A01M 1/103 |
| GB | 2463953 | A * | 4/2010 | ............ | A01M 1/026 |
| JP | 08131042 | A * | 5/1996 | | |
| JP | 08-322446 | * | 10/1996 | | |
| JP | 2000139318 | A * | 5/2000 | | |
| JP | 2000189030 | A * | 7/2000 | | |
| WO | WO 9944417 | A2 * | 9/1999 | ............ | A01M 1/023 |

* cited by examiner

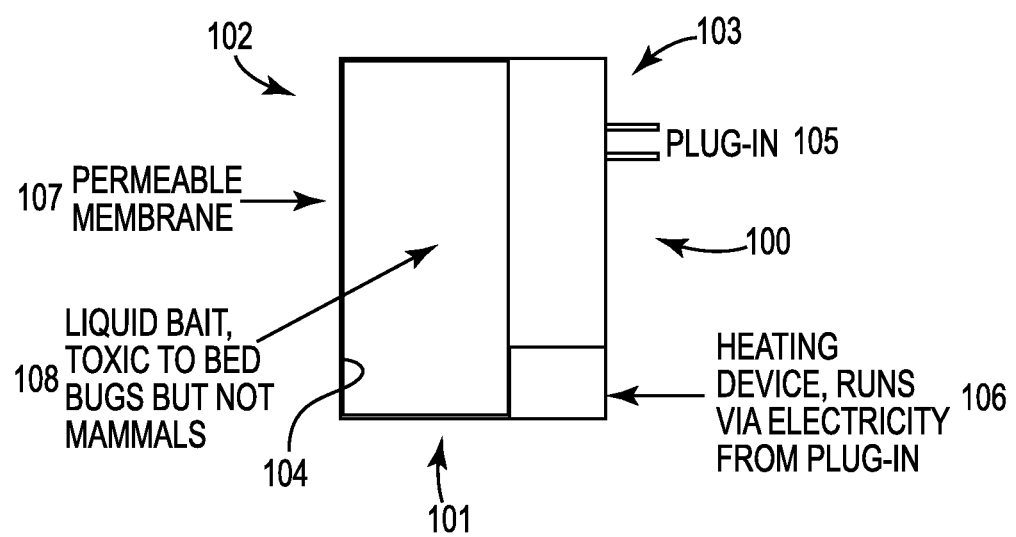

METHOD OF USING INSECT BAIT STATION

CROSS-REFERENCE TO RELATED APPLICATIONS

This application claims priority to U.S. Provisional Application Ser. No. 61/074,266 filed on Jun. 20, 2008 and entitled "Insect Bait Station" and is a divisional of U.S. patent application Ser. No. 12/486,918 filed on Jun. 18, 2008, now U.S. Pat. No. 9,089,122, the disclosures of which are incorporated herein by reference.

FIELD OF THE INVENTION

The present invention relates to insect bait stations and to bait stations for piercing and sucking insects, particularly blood-feeding insects, and more particularly, bed bugs.

BACKGROUND OF THE INVENTION

Bed bugs are relatively small insects, approximately ¼ inch long and less than ¼ inch wide that feed on the blood of animals, including humans. They have piercing-sucking mouthparts (similar to a mosquito) that mandate the way they consume blood from their hosts. The species *Cimex Lectularus* is the most common worldwide.

Bed bug infestations typically originate by bed bugs being carried to a new location. Bed bugs are able to cling onto objects and hide in small spaces so they may be easily transported in travelers' belongings. As a result, locations such as hospitals, nursing homes, hotels, apartments, military barracks, dormitories, cruise ships, movie theaters, and other buildings with relatively high turnover are more vulnerable to bed bug infestations. Although once eradicated in the United States by the use of DDT and other chemicals no longer in use, the increase of international travel has contributed to the resurgence of bed bugs in the United States.

Bed bugs can live for relatively long periods of time without feeding. Therefore, infestations are not likely to be eliminated simply by leaving a location unoccupied for an extended period of time. Bed bugs are typically active at night and primarily hide during the day in tiny cracks or crevices. Bed bugs may establish harborage in furniture, along baseboards, in upholstery, in carpeting, and in countless other places. Multiple stages of bed bugs often aggregate in groups but do not divide labor among individuals (as in a caste system) similar to some social insect species.

There are many aspects of bed bug biology that make them difficult to eradicate once they have established a presence in a location. The present invention addresses the problems associated with the prior art devices and provides for an effective bait station.

SUMMARY OF THE INVENTION

One aspect of the present invention provides for unique liquid bait that is nontoxic to humans. In another aspect of the invention, the liquid bait is in a container such as a pouch, at least a portion of which may be pierced by at least one insect. In another aspect, the invention provides a device for exterminating blood-feeding insects, comprising a self-sealing membrane, the membrane containing a solution toxic to the blood-feeding insects. In another aspect of the invention, the liquid bait is provided in a container such as a shallow tray that may be comprised of plastic. The plastic container is then sealed with the pierceable membrane.

Another aspect of the present invention provides for novel liquid bait. The liquid bait is comprised of a base and an optional active ingredient. The base is comprised of a solution of sodium chloride in water, phosphate buffer, citric acid in water, or sodium lauryl sulfate in water. The optional active ingredients are selected from the group comprising boric acid, citric acid, indoxacarb, chlorphenapyr, sodium lauryl sulfate, deltamethrin, lamda cyhalothrin, and fipronil. Preferably, the liquid bait has a pH of between about 6 and 8. In another embodiment, the liquid bait has a pH of between about 7 and 8, and in another embodiment has a pH of about 7.4.

In an alternate embodiment, the base is comprised of sodium chloride diluted in water. An up to about 70 wt % solution sodium chloride in water can comprise the base. Up to about 12 wt % sodium chloride in water solution may be used as the base or from about 6 wt % up to about 12 wt % sodium chloride in water. Such a base is particularly desirable due to the fact that it is virtually harmless to humans and because it is inexpensive. Any of the previously mentioned optional active ingredients may be added when the sodium chloride solution is used as the base. However, as surprisingly discovered, additional ingredients are not necessary for lethality.

Another aspect of the present invention provides for including an attractant such as, but not limited to, pheromones, food attractants, tactile cues, heat, carbon dioxide, water, and olfactory cues.

Another aspect of the present invention provides for a housing including a heating element, the heating element heating the liquid bait contained within the membrane contained within the housing.

Another aspect of the invention provides for a housing to allow an insect's mouthparts to puncture the membrane without requiring the insect's feet or other body parts to contact the membrane.

Another aspect of the present invention provides for a method of attracting and killing insects, in other words, controlling blood-feeding insects comprising heating liquid bait contained in a pouch to approximately 75 to 130° F.

Another aspect of the present invention provides for monitoring insect activity such as, but not limited to, visual inspection, an indicator light, an electronic signal, a counter, a powder or a liquid detectable either visually or with the aid of a UV light or other detection method, a visual indication that the membrane has been pierced, an ingredient in the liquid bait that changes color when an insect has fed on it, and a pressure sensitive element or thermochromic ink could be included that changes color when an insect has contacted it.

BRIEF DESCRIPTION OF THE DRAWINGS

FIG. 1 is a schematic view of an insect bait station constructed according to the principles of the present invention.

DETAILED DESCRIPTION OF SOME PREFERRED EMBODIMENT

The term, "controlling" as used herein refers to monitoring and/or exterminating blood feeding insects such as bed bugs. The term, "active ingredient" as used herein refers to any chemical or substance having either attractant or toxicant properties for insects. "Active ingredients" include but are not limited to boric acid, citric acid, sodium lauryl sulfate, indoxacarb, chlorphenapyr, deltamethrin, lamda cyhalothrin, and fipronil or any combination thereof.

As used herein, weight percent (wt-%), percent by weight, % by weight, and the like are synonyms that refer to the concentration of a substance as the weight of that substance divided by the total weight of the composition and multiplied by 100.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

A preferred embodiment insect bait station or exterminating device constructed according to the principles of the present invention is designated by the numeral 100 in the drawings Although the preferred embodiment is described for use with bed bugs, it is recognized that the insect bait station 100 could be used with other types of piercing and sucking insects, otherwise referred to as blood-feeding insects. Examples of other blood-feeding insects include the sandfly, blackfly, tsetse fly, assassin bug, mosquito, tick, louse, mite, midge, chigger, flea.

The insect bait station 100 or exterminating device preferably includes a housing 101 having a front 102 and a rear 103 defining a cavity 104 there between. The rear 103 preferably includes a plug 105 extending outward from the rear 103, and the plug 105 is configured and arranged to fit into an electrical outlet (not shown). The plug 105 is operatively connected to a heating device 106, which heats when the plug 105 is connected to the electrical outlet. The front 102 preferably includes an opening (not shown) allowing access to a pouch 107 configured and arranged to fit within the cavity 104. The top of the housing 101 preferably includes an opening (not shown) through which the pouch 107 may be slid into and out of the cavity 104. The heating device 106 heats the pouch 107 and liquid bait 108 contained within the pouch 107 to approximately 75 to 130° F., 80 to 120 degrees F., 90 to 110 degrees F. As may be appreciated, it is desirable to mimic the body temperature of the warm blooded animal upon which the blood-feeding insect feeds, or in other words, to mimic the body temperature of the host.

The insect bait station 100 acts as an artificial host, attracting insects so that the insects feed on the liquid bait 108 contained within the pouch 107. In one embodiment of the invention, at least a portion pouch 107 is comprised of a membrane that is pierceable by blood feeding insects. In another embodiment, membrane is sufficiently re-sealable or is self-sealing. At least a portion of the pouch 107 should be at least a sufficiently thin to allow piercing by bed bug mouthparts. To feed on the liquid bait 108, the bed bugs prefer a warm liquid housed within a membrane. The membrane could be made of PARAFILM™ film or any other suitable material that is pierceable and optionally self-sealing so that the membrane does not leak any liquid after piercing by the bed bugs. Liquid that could leak from the pouch 107 includes the liquid bait 108 and any saliva injected into the pouch 107 by the insects. Parafilm™ is a product available from Alcan Packaging located in Chicago, Ill. Parafilm™ is commonly used for sealing or protecting vessels (such as flasks or cuvettes). It is stretchable, moldable, waterproof, odorless, thermoplastic, semitransparent and self-adhering. Parafilm™ is a wax-blended polyolefin film, and is one example of a type of film that could be used in the present invention as the pierceable membrane.

The membrane containing the toxic solution or bait may also be formed of natural or artificial collagen film. Ham wrap or lamb skin are suitable examples of films for the membrane. Other examples of film suitable for forming the membrane of the invention include but are not limited silicone film and Baudruche film. The membrane must be sufficiently thin to allow an insect to pierce or puncture the membrane. Any substrate that allows piercing or punctures by the mouthparts of a blood-feeding insect and is optionally sufficiently self-sealable to contain the liquid bait is suitable for holding the toxic solution of the present invention. In a preferred embodiment, the inventors have found that such a membrane is less than about 5.0 mils thick. It is recognized that a material that may not be originally thin enough for an insect to pierce, may be stretched to form a sufficiently thin membrane for the purposes of the invention.

The liquid bait 108 could be any suitable solution that preferably attracts and/or kills the insects after consumption. Preferably, the liquid bait 108 includes an attractant and a toxicant. The attractant could be sensed through the membrane, and heating the liquid bait 108 assists in attracting insects. Any method suitable for heating liquids may be employed in the present invention. These include battery-operated heaters, chemical heaters whereby two chemicals remain separate until an exothermic reaction is desired such as in glove and boot warmers, or an electric heating device.

Depending upon the desired end result, the liquid bait 108 optionally includes 0 to 10% additional active ingredient(s) such as boric acid, preferably 10% boric acid, and a phosphate buffer, preferably with a pH of 6 to 8, and more preferably with a pH of 7.4, in solution so piercing and sucking insects can feed on it. The liquid bait 108 preferably has a pH of between about 6 to about 8. Consumption of boric acid is toxic to many species of insects. Other additional active ingredients could be used such as indoxacarb, chlorphenapyr, deltamethrin, lamda cyhalothrin, citric acid, and fipronil. One skilled in the art will appreciate that any of these may be used alone or in combination with others.

The liquid bait 108 may optionally include 0 to 10% additional active ingredient(s). The liquid bait along with the active ingredient(s) preferably has a pH of between about 6 and 8, and more preferably has a pH of 7.4, so piercing and sucking insects can feed on it.

The bait station attracts bed bugs by including an attractant such as, but not limited to, pheromones, food attractants, tactile cues, heat, carbon dioxide, and olfactory cues. Such attractants are described in U.S. Patent Application Publication No. 2007/0044372 A1, which is incorporated herein by reference in its entirety for all purposes.

The bait station kills or controls bed bugs by monitoring by including a toxic ingredient. In order to allow blood-feeding insects to ingest the bait, the bait is preferably provided in solution. The liquid bait solution is comprised of a base and an optional active ingredient. The base is selected from the group consisting of sodium chloride in water, phosphate buffer, citric acid in water, or sodium lauryl sulfate in water. The inventors have surprisingly found that any of these solutions is deadly to bed bugs at various concentrations.

The inventors have surprisingly found that the base solutions are lethal to bed bugs. This is surprising because many of the base solutions are relatively benign to humans. Without being bound by theory, it is believed that ingesting the base solution upsets the ionic balance within the insect's body proving deadly. It is believed that the base solutions mimic the taste of blood thereby increasing the likelihood that bed bugs will feed upon the solution. Sodium chloride solution in water is a particularly desirable base solution for bedbugs because it is not toxic to humans and is therefore an Environmental Protection Agency exempt product. An additional benefit is the low cost of using a solution of sodium chloride in water since both components are relatively inexpensive.

Solutions of up to about 70 weight percent sodium chloride in water are useful as bait in the present invention. In some embodiments from about 0.5 weight percent up to about 30 weight percent, from about 5 to 15 weight percent, and from about 6 to about 12 weight percent are efficacious at killing bedbugs. Bed bugs fully engorge themselves upon solutions of sodium chloride and water up to 5 weight percent, but death was recorded from solutions up to 70 weight percent just from bed bugs "tasting" the toxic solutions. Again, without being bound by theory, it is believed that the higher percentage sodium chloride solution, that is greater than 70 percent NaCl, is less effective because the bed bugs refused to feed upon the solution.

In an embodiment the device of the invention provides a housing or some other aspect external to the membrane to allow blood-feeding insects to puncture or feed from the bait or toxic solution without requiring the insect to otherwise contact the membrane with other body parts. Such a housing can be in the form of a cage or shell into which the solution-containing membrane pouch may be placed. It is assumed that bed bugs in particular are attracted to and choose to feed from mammals based on the heat they emit, but post-consumption of the blood meal; they are immediately repelled by higher temperatures. When feeding in their environment bed bugs prefer to feed off the host. They are able to puncture a host's skin while standing upon clothing, bedding or upholstered furniture thereby never requiring the bed bug to contact a human's skin. The invention is designed to mimic this "natural" feeding behavior thereby allowing the bed bug to stand on a housing, cage, shell, netting, or shelf or other architecture external to the membrane yet still allowing the bedbug to puncture the membrane and feed upon the bait or toxic solution. In an embodiment at least a portion of the membrane may be encased in a permeable fabric such as cheesecloth, for example. Such a permeable fabric would allow an insect's mouthparts to penetrate the fabric while providing a stable platform to maintain the insect away from the surface of the membrane.

In an embodiment, the housing or external shelf provided to allow the insect to feed without otherwise contacting the membrane, is textured. Any texture desirable to bedbugs may be employed in the present invention. Such texturing may mimic that of fabric such as upholstery, bedding or clothing. The texturing may mimic components commonly used in upholstered furniture such as batting, foam, ticking, cording, including natural or man-made fibers, or wood. It is envisioned that the housing may be fashioned from plastic thereby allowing such texturing of the surface. In the event that fabric is provided as the housing to support the insect, no additional texturing would be necessary.

In an embodiment, the toxic solution or bait is placed into a plastic container and the container is sealed with the membrane. The plastic container may be formed via injection molding and may be in the form of a shallow tray similar to a condiment or disposable jelly container. The bait or liquid solution is then placed into the reservoir of the tray and the membrane is then used to cover or seal the tray opening. Such a tray could be inserted into the housing or cage described above. Such a design would allow for the housing or cage to be re-used and would allow for refilling or reloading of the bait once the liquid bait or solution is spent.

In another embodiment the liquid bait or solution may be placed into a refillable reservoir housed within the previously described casing or housing. The refillable reservoir may include a tube or other opening into which the liquid bait may be poured. The refillable reservoir will also include a portion sealed by the pierceable membrane to allow insects to feed through the membrane. Such an embodiment would provide for a reusable and refillable bait station.

The bait station preferably also allows for monitoring insect activity. Visual inspection, seeing insects on the bait station, could be used. A light could be activated and illuminated when an insect is detected. An electronic signal or a counter could be activated when an insect is detected. A powder or a liquid could be included on the bait station that the insects will track to other locations and that are detectable either visually or with the aid of a UV light or other detection method. For example, the exterior of the device could include an ultraviolet dye such as those commercially available from Day Glo Color Corporation located in Cleveland Ohio in the form of a powder, liquid or other readily transportable form. When an insect contacts the dye, it would carry the dye with it, thereby providing evidence that it has contacted the device. Movement of the dye away from the device would be apparent once ultraviolet rays were shined in the general area of the device. Additionally or alternatively the membrane could provide visual indication that it has been pierced. The liquid bait could include an ingredient that changes color when an insect has fed on it. For example, bed bugs' saliva contains nitric oxide, and bed bugs inject saliva prior to feeding, so the liquid bait could react to the accumulation of nitric oxide, changing gradually as more nitric oxide accumulates. A pressure sensitive element could be included that changes color when an insect has contacted it. Other monitoring/sensing techniques are also described in U.S. Patent Application Publication No. 2007/0044372 A1, which is incorporated in its entirety herein by reference for all purposes.

Dyes suitable for use in coloring the toxic solution or bait include but are not limited to calco red, oil soluble blue II, and rhodamine. One skilled in the art will appreciate that any of these may be used alone or in combination with others.

In addition, the bait station has a discrete design. The bait station could resemble a GLADE™ PLUGIN™ Air Freshener and could be disguised as such. Alternatively, the bait station could resemble a power strip with a cord that plugs into an outlet. A portion of the power strip could include the bait station and several outlets could be included for other uses. Further, because the insects are not trapped and typically die at a different location, the dead insects will not accumulate proximate the bait station and call attention to the bait station.

The bait station of the present invention allows for proactive and discreet monitoring and killing of insects, even at low levels of infestation. Thus, the risk of infestation and re-occurrence of infestation is reduced.

A method of controlling blood-feeding insects is disclosed. The method includes providing liquid bait in a self-sealing membrane and allowing blood-feeding insects to feed from the bait. The liquid bait may contain a lethal or toxic solution, or may simply provide a means of attracting the insects for the purpose of monitoring their activity. In an embodiment the liquid bait is toxic and may include an optional active ingredient. The active ingredient may serve as an insecticidal agent or may simply act as an attractant. The method may further include additional attractants such as pheromones that may or may not be contained within the liquid bait or heat.

The invention will now be further exemplified by the following Examples.

EXAMPLES

For the following Examples an artificial membrane feeding station was prepared and used. The feeding station had a sealed container sealed with stretched Parafilm™. The Parafilm™ was stretched to <5.0 mils thick. The liquid bait identified in the various Examples below was placed in the sealed container.

Example 1

Boric acid is an insecticidal dust that causes death upon consumption by most insects with chewing mouthparts. Bed bugs have blood-feeding, piercing/sucking mouthparts that limit their ability to pick up and consume the insecticidal dust in its powder form. To determine whether consumption of boric acid kills bed bugs, several mixtures of boric acid and phosphate buffer, DUPONT™ ADVION™ fire ant bait including indoxacarb and phosphate buffer, and just phosphate buffer solutions were made. Phosphate buffer solutions having a pH of 5.2 and a pH of 7.4 were tested, and only the phosphate buffer solution having a pH of 7.4 was ingested by the bed bugs. Multiple groups of ten bed bugs fed on the solutions via artificial membrane feeding systems as described above, and post-consumption mortality was recorded.

In one test, the artificial feeding systems included the following eight solutions: a first control solution including approximately 5 milliliters of human blood, a second control solution including approximately 5 milliliters of phosphate buffer (pH 7.4), a first test solution including approximately 9.5 milliliters of phosphate buffer (pH 7.4) and 5 grams of BORID™ boric acid powder, a second test solution including approximately 9.0 milliliters of phosphate buffer (pH 7.4) and 1.0 grams of BORID™, a third test solution including approximately 4.95 milliliters of phosphate buffer (pH 7.4) and 0.05 grams of BORID™ boric acid powder, a fourth test solution including approximately 4.90 milliliters of phosphate buffer (pH 7.4) and 0.10 grams of BORID™ boric acid powder, a fifth test solution including approximately 4.95 milliliters of phosphate buffer (pH 7.4) and 0.05 grams of DUPONT™ ADVION™ fire ant bait, and a sixth test solution including approximately 4.90 milliliters of phosphate buffer (pH 7.4) and 0.10 grams of DUPONT™ ADVION™ fire ant bait. The BORID™ boric acid powder and the DUPONT™ ADVION™ fire ant bait were dissolved into the phosphate buffer solution by heating the ingredients in a microwave for approximately 30 seconds. Each solution was offered to ten bed bugs. After approximately 30 minutes, the engorged (fed to completion) bed bugs were transferred to new containers. Mortality was recorded every 24 hours for 4 days.

The results showed 100% efficacy within 24 hours on bed bugs that consumed the solution containing 0.05 grams boric acid and 4.95 milliliters of phosphate buffer having a pH of 7.4. Some mortality (approximately 70%) was recorded within 24 hours for the bed bugs that consumed the phosphate buffer solution without boric acid, the second control solution. Mortality was not significantly different for the solution including DUPONT™ ADVION™ fire ant bait including indoxacarb compared to the phosphate buffer control, but this could be because it was harder to get the DUPONT™ ADVION™ fire ant bait into solution so it was less likely the bed bugs consumed the DUPONT™ ADVION™ fire ant bait.

In conclusion, the phosphate buffer (pH 6 to 8) with a 0 to 10% additional ingredient(s), heated to 75 to 130° F. in a membrane will attract and kill adult insects such as bed bugs.

Example 2

This Example illustrates bed bug mortality when exposed to solutions containing minimum risk pesticides. Minimum risk pesticides are a special class of pesticides that are not subject to federal registration requirements because their ingredients, both active and inert, are demonstrably safe for the intended use. Minimum risk pesticides that meet certain criteria are exempt from federal registration under section 25(b) of the Federal Insecticide, Fungicide, and Rodenticide Act (FIFRA) incorporated herein by reference in its entirety for all purposes. The U.S. Environmental Protection Agency (EPA) does not review or register pesticides that satisfy the 25(b) criteria, though registration is required by most states.

To determine whether consumption of ingredients listed under section 25(b) of the Federal Insecticide, Fungicide, and Rodenticide Act kills bed bugs, several mixtures of salt, citric acid, potassium sorbate, sodium lauryl sulfate (SLS), castor oil, sesame oil, cinnamon oil, garlic oil, citronella oil, lemongrass oil, peppermint oil, cedar oil, clove oil, rosemary oil, thyme oil, geranium oil, geraniol, and flaxseed oil were made. Oil based solutions were dissolved into 2% sodium lauryl sulfate ("SLS") and water mixtures. Remaining ingredients were dissolved in water. Concentrations of 1%, 5%, and 50% of each solution were made. Control solutions consisted of either human blood or water depending on the test solutions in each experiment. Groups of twenty bed bugs were offered each solution via the artificial membrane feeding system described above for 60 minutes. After 60 minutes, the containers of 20 bed bugs were removed from the feeding station and the number that fed to completion was recorded. Post-exposure mortality was recorded at 24 hours and 120 hours after exposure to the active solution.

The results showed 0% efficacy within 120 hours for bed bugs that consumed potassium sorbate, citronella oil, peppermint oil, clove oil, rosemary oil, and flaxseed oils solutions. Results showed some efficacy against bed bugs that were exposed to lower concentrations of sodium chloide, SLS, citric acid, castor oil, sesame oil, cinnamon oil, garlic oil, lemongrass oil, cedar oil, thyme oil, geranium oil, and geraniol oil solutions. The highest observed levels of efficacy against bed bugs were for those exposed to sodium chloride, SLS, and citric acid solutions. However, solutions of SLS degraded the Parafilm™ membrane used for each of the test solutions.

In conclusion, active solutions containing various concentrations of sodium chloride or citric acid are preferred choices for an active ingredient based on the levels of mortality recorded within 120 hour of exposure compared to the remaining contents described on the 25b list pertaining to minimum risk pesticides.

Example 3

This Example illustrates the mortality of bed bugs exposed to varying concentrations of sodium chloride dissolved in water. Example 2 indicated that mortality occurred in groups of bed bugs exposed to solutions containing various concentrations of sodium chloride. However, not all cases of mortality correlated with engorgement (feeding to completion).

To determine optimum concentrations of sodium chloride solutions (for both feeding and mortality), bed bugs were offered the following concentrations sodium chloride diluted in water on a weight percent basis: 0, 0.05, 0.25, 0.5%, 1%, 2%, 3%, 4%, 5%, 6%, 7%, 8%, 9%, 10%, 12%, 14%, 16%, 18%, 20%, 25%, 30%, 35%, 40%, 50%, 60%, 70%, 80%, 90%, and 100%. Each solution was offered to groups of 10-20 bed bugs via the artificial feeding stations described above. After approximately 60 minutes, the containers of 10-20 bed bugs were removed from the feeding station and the number that fed to completion was recorded. Post-exposure mortality was recorded at 4 hours, 24 hours and/or 48 hours after exposure to the active solution.

The results showed that bed bugs feed to completion or engorge upon solutions containing up to 5% sodium chloride. However, some level of mortality was reported in all sodium chloride solutions up to 70% wt. sodium chloride, indicating that although the bed bugs did not consume large quantities of the solution, apparently, "tasting" the active was enough to cause high levels of mortality. The highest levels of mortality (up to 70%) was recorded from solutions containing 6-12% wt. sodium chloride. Without being bound by theory the inventors believe that 0 wt. %-5 wt. % concentration of sodium chloride in water best mimics the concentration found in blood. However, notwithstanding the preference for the 6-12% NaCl solution, solutions from 0.5% up to about 70% by weight sodium chloride in water were effective at exterminating bed bugs.

In conclusion, active solutions containing concentrations between about 6 wt. % and about 12 wt. % sodium chloride are preferred choices for a base according to the levels of mortality recorded within 48 hour of exposure compared to the remaining concentrations of sodium chloride tested against.

Example 4

In this Example, the efficacies of various sodium chloride solutions having 5% boric acid added were tested. In the previous example, we identified optimum concentrations of sodium chloride solutions that resulted in mortality of bed bugs. However, we had observed higher mortality when bed bugs were offered solutions of phosphate buffer and boric acid in Example 1.

To determine if boric acid enhanced mortality of sodium chloride base solutions, 5 weight % boric acid was added to various concentrations of sodium chloride dissolved in water. Bed bugs were offered the following concentrated solutions of sodium chloride 0%, 2%, 4%, 6%, 8%, 10%, and 12% with and without the addition of 5% boric acid. Each solution was offered to groups of 20 bed bugs via the artificial feeding stations described above. After approximately 60 minutes, the containers of 20 bed bugs were removed from the feeding station and the number that fed to completion was recorded. Post-exposure mortality was recorded at 4 hours, 24 hours and/or 48 hours after exposure to the active solution.

The results showed that the addition of 5% boric acid significantly enhanced mortality compared to sodium chloride base solutions without boric acid. We observed levels of mortality between 10%-55% for each of the sodium chloride base solutions tested. These results were similar to previous findings described in Example 3. However, we observed a 25-60% increase in mortality when 5% boric acid was added to the sodium chloride solution. The highest level of mortality (75%) was observed in the solution containing 8% sodium chloride and 5% boric acid.

In conclusion, active solutions containing concentrations between about 6% and about 12% sodium chloride with about 5% boric acid are preferred choices for an active ingredient based on the levels of mortality recorded within 48 hours of exposure compared to sodium chloride solutions without boric acid.

Example 5

Various materials were tested to determine whether or not bed bugs could effectively feed through the membrane and ingest the bait. Materials tested are provided in Table 1 below. Human blood was used as bait in this Example because it was most readily accepted by the bed bugs. The thickness of the tested materials in mils is also provided in Table 1 along with whether or not bed bugs fed through the material. It was undetermined whether or not the material or the thickness, or combinations of both were the determinative of whether or not bed bugs fed through the material.

TABLE 1

| Thickness (mil) | Material | Fed Through? |
|---|---|---|
| 0.84 | Collagen ham wrap | Yes |
| 0.68 | Lamb skin | Yes |
| 3.5 | Stretched Parafilm ™ | Yes |
| 2.0 | Stretched Parafilm ™ | Yes |
| 1.5 | Super Stretched Parafilm ™ | Yes |
| Unmeasured | SARAN ™ food wrap film | No |
| Unmeasured | GLAD ™ Press N' Seal ™ | No |
| Unmeasured | Stretched GLAD ™ Press N'Seal ™ | No |
| 5.0 | Unstretched Parafilm ™ | No |
| Unmeasured | Unstretched Parafilm ™ under super stretched Parafilm ™ | No |

The above specification, examples and data provide a complete description of the manufacture and use of the composition of the invention. Since many embodiments of the invention can be made without departing from the spirit and scope of the invention, the invention resides in the claims hereinafter appended.

We claim:

1. A method of controlling blood-feeding insects, comprising:
   providing a device comprised of a membrane;
   the membrane containing a solution toxic to blood-feeding insects; the solution comprising a base; the base consisting of between about 6 and 12 wt % NaCl in water, and optionally further consisting of citric acid and/or sodium lauryl sulfate; wherein the solution has a pH of between about 6 and 8; and
   allowing the insects to feed from the device.

2. The method of claim 1 further comprising heating the solution to between about 80 and 120 degrees F.

3. The method of claim 1 wherein the membrane is less than 5.0 mils thick.

4. The method of claim 1 wherein the membrane is comprised of wax-blended polyolefin film, natural collagen film, or artificial collagen film.

5. The method of claim 1 wherein the membrane is comprised of wax-blended polyolefin film.

6. The method of claim 1 further comprising a heat source to heat the solution to between about 80 and 120 degrees F.

7. The method of claim 6 wherein the heat source generates heat from being plugged into an electrical outlet.

8. The method of claim 1 wherein the membrane is self-sealing.

9. The method of claim 1 wherein the pH of the solution is between about 7 and 8.

10. The method of claim 1 wherein the membrane includes an indicator dye to identify when an insect has fed from the device.

11. The method of claim 1 wherein the solution further comprises a dye.

12. The method of claim 11 wherein the dye is selected from the group consisting of calco red, oil soluble blue II, and rhodamine B.

13. The method of claim 1 further comprising a source for releasing an attractant.

14. The method of claim 13 wherein the attractant is comprised of carbon dioxide, water, or pheromones.

15. The method of claim 1 further comprising a housing to allow an insect's mouthparts to puncture the membrane without requiring the insect's feet or other body parts to contact the membrane.

16. The method of claim 15 wherein the housing comprises a shelf.

17. The method of claim 1 wherein the membrane is textured.

18. The method of claim 15 further comprising a dusting of fluorescent dye on the housing and membrane.

19. The method of claim 1 wherein the base further consists of boric acid, citric acid, sodium lauryl sulfate, indoxacarb, chlorphenapyr, deltamethrin, lamda cyhalothrin, or fipronil or any combination thereof.

\* \* \* \* \*